(12) United States Patent
Bhaskaran et al.

(10) Patent No.: US 7,507,421 B2
(45) Date of Patent: Mar. 24, 2009

(54) HYDROXYCITRIC ACID SALT COMPOSITION AND METHOD OF MAKING

(75) Inventors: Sunil Bhaskaran, Wanorie (IN); Sevanti Mehta, Houston, TX (US)

(73) Assignee: Unibar Corporation, Houston, TX (US)

( * ) Notice: Subject to any disclaimer, the term of this patent is extended or adjusted under 35 U.S.C. 154(b) by 883 days.

(21) Appl. No.: 10/425,428

(22) Filed: Apr. 29, 2003

(65) Prior Publication Data

US 2003/0207942 A1 Nov. 6, 2003

Related U.S. Application Data

(60) Provisional application No. 60/376,490, filed on Apr. 30, 2002.

(51) Int. Cl.
| | |
|---|---|
| *A61K 47/00* | (2006.01) |
| *A61K 9/00* | (2006.01) |
| *A61F 2/00* | (2006.01) |
| *A23K 1/17* | (2006.01) |
| *A61K 36/00* | (2006.01) |

(52) U.S. Cl. .................. 424/439; 424/400; 424/426; 424/442; 424/725; 514/772

(58) Field of Classification Search .................. 424/400, 424/439
See application file for complete search history.

(56) References Cited

U.S. PATENT DOCUMENTS

| | | | |
|---|---|---|---|
| 5,656,314 A | 8/1997 | Moffett et al. | |
| 5,783,603 A | 7/1998 | Majeed et al. | |
| 6,160,172 A * | 12/2000 | Balasubramanyam et al. | |
| 6,207,714 B1 | 3/2001 | Clouatre et al. | |
| 6,221,901 B1 | 4/2001 | Shrivastava et al. | |
| 7,063,861 B2 * | 6/2006 | Majeed et al. | 424/451 |

FOREIGN PATENT DOCUMENTS

| | | | |
|---|---|---|---|
| WO | 99/03464 | * | 1/1999 |
| WO | WO99/03464 | | 1/1999 |

OTHER PUBLICATIONS

PCT International Search Report, PCT/US03/13173 dated Aug. 14, 2003, 1 p.
Tyler Standard Screen Scale, C.J. Geankoplis, *Transport Processes and Unit Operations*, Allyn and Bacon, Inc., Boston, MA, p. 837, (1978).
P. Kucera et al., *Differential Frontal Analysis of Carboxylic Acids*, J. Chromatography (1981) 210:373-388 (9 p.).
US Environmental Protection Agency, *Acute Oral Toxicity (Guideline 425) Statistical Program*, OECD Guideline For the Testing of Chemical, May 2001, pp. 1-27 http://www.oecd.org/dataecd/19/57/1839830.pdf.

* cited by examiner

*Primary Examiner*—Humera N Sheikh
(74) *Attorney, Agent, or Firm*—Conley Rose, P.C.

(57) ABSTRACT

Disclosed is a hydroxycitric acid salt composition comprising calcium and potassium salts of hydroxycitric acid, preferably in a defined proportion which yields a very pure, stabilized preparation that is substantially tasteless for optimal use in a variety of foods items. The HCA salts are prepared by a process that includes treating an aqueous extract of *Garcinia cambogia* or *Garcinia indica* fruit with a liquid quaternizing agent such as a trialkylamine in which the alkyl groups are octyl, caprylyl, isooctyl, lauryl or decyl.

5 Claims, 2 Drawing Sheets

HYDROXYCITRIC ACID SALT COMPOSITION AND METHOD OF MAKING

CROSS-REFERENCE TO RELATED APPLICATIONS

This application claims the benefit under 35 U.S.C. § 119 (e) of U.S. Provisional Patent Application No. 60/376,490 filed Apr. 30, 2002, the disclosure of which is hereby incorporated herein by reference.

STATEMENT REGARDING FEDERALLY SPONSORED RESEARCH OR DEVELOPMENT

Not applicable.

BACKGROUND OF THE INVENTION

1. Field of the Invention

The present invention generally relates to hydroxycitric acid (HCA) and its salts, and more specifically to water soluble mixtures of calcium and potassium salts of HCA, and to methods of making the calcium and potassium salts and mixtures thereof. The invention also relates to the use of such compositions as nutraceuticals or dietary supplements.

2. Description of Related Art

The fruit acid hydroxycitric acid (HCA) is a naturally occurring fruit acid found in the rinds of the fruit of *Garcinia cambogia*, *Garcinia indica* and *Garcinia mangostana*. The identification of the acid, methods of isolation and analytical methods for estimating concentration were elucidated by Y. S. Lewis et al. in METHODS OF ENZYMOLOGY (Academic Press, N.Y. (1969)). Hydroxycitric acid has been investigated for its nutritional importance, and studies have shown that pharmacologic amounts of HCA can accelerate metabolism, leading to weight loss, improved glucose metabolism, can suppress the appetite, and can produce other physiological effects. Various researchers have evaluated HCA for its weight control properties, fat burning properties, lipid level lowering effect, appetite regulation, metabolic rate increase, and other effects. A number of U.S. patents have been granted based on the results of those studies and on various methods of extracting HCA from the Garcinia fruit. For example, U.S. Pat. No. 5,656,314 (Moffett et al.) describes a certain hydroxycitric acid concentrate and food products prepared therefrom. By that method, free hydroxycitric acid having a concentration ranging from 23 to 54% in aqueous media is obtained.

It has been found, however, that the free acid form of HCA is unstable, forming lactones which generally do not possess the desired bioactivity. Therefore, food preparations that incorporate the free acid in liquid form will not provide the full benefit of the functional product (i.e., HCA) in the final preparation. The liquid form of free HCA tends to be unstable during storage, so it may not be the optimal form for incorporation of HCA in food products.

In U.S. Pat. No. 5,783,603 (Majeed et al.) administration of potassium hydroxycitrate for the suppression of appetite and induction of weight loss is disclosed. This salt is prepared by treating Garcinia-extracted HCA with methanolic potassium hydroxide, and the potassium salt of HCA is dried under vacuum. In powder form, potassium hydroxycitrate is very hygroscopic in nature, and typically has very poor keeping qualities. Another drawback of this type of preparation is that the assay of HCA may be too low for some applications.

U.S. Pat. No. 6,160,172 (Balasubramaniam et al.) describes certain compositions containing soluble double metal salts of hydroxycitric acid. Group IA and IIA (i.e., Li, Na, K, Rb, Cs, Fr, Be, Mg, Ca, Sr, Ba and Ra) salts of HCA are formed as powders after precipitating the Garcinia-extracted HCA solution with polar solvents. This process can contain solvent residues and high levels of chlorides in the final product, however. Potential contaminants such as chloride and oxalic acid limit application of the product where the original taste, color and fragrance of the base material, such as a food or beverage, cannot be compromised. Another drawback of a method such as this is that it can be quite cumbersome due to the number of steps.

U.S. Pat. No. 6,207,714 (Clouatre et al.) describes the use of commercially available pharmaceutical preparations of a calcium, magnesium, potassium or sodium salt of hydroxycitric acid for increasing a person's glucose metabolism.

U.S. Pat. No. 6,221,901 (Shrivastava et al.) describes a method of making a purified magnesium hydroxycitrate preparation, and discusses its use as a medicament for treating cardiovascular disease. No food supplementation or body weight effects were noted in rabbits that were fed the magnesium hydroxycitrate preparation.

It is well known that hydroxycitric acid is unstable in its free acid form, so it is typically prepared as its salt for stability and for use in any of the applications mentioned above. Some commercially available and commonly used salts include calcium salts of HCA standardized for 50%, 55% and 60% levels of HCA. The potassium salt form is also readily available as a 45%, 50%, 55% and 60% salt. One drawback of typical commercially available calcium HCA salt preparations is that they are not very soluble in water. This severely limits its applicability for use in drinking water, beverages, ice cream, candies and in food. Another disadvantage of most calcium salts of HCA that are available today is that they typically deliver only a maximum assay of 60%, thereby limiting the total availability of HCA in any composition.

The potassium salt of HCA overcomes the major disadvantage of the calcium salt (i.e., insolubility) due to the good water solubility of the potassium salt of HCA. However, due to the high level of potassium in the salt, the potassium salt leaves a strong pungent taste of potassium. This tends to interfere with the taste profile of the food, or beverage, which limits the amount of potassium hydroxycitrate that can be incorporated into a food to levels that are below the amount needed to achieve the desired functional effects of the HCA in the recipient. Another disadvantage often encountered with the potassium salt is a tendency to form lumps during storage due to its highly hygroscopic nature, thus reducing the shelf life of the HCA salt. Commercial manufacture is also made cumbersome due to the undesirable hygroscopic property. The assay of HCA in conventional potassium hydroxycitrate preparations is also typically low, at 60% or less.

PCT Published Patent Application No. WO 99/03464 (Raju) describes certain hydroxycitric acid compositions containing 40% or more HCA, 5-13% calcium and about 9-20% potassium or about 5-10% sodium for use as dietary supplements and food products to reduce body weight. Hydroxycitric acid lactone content is said to be less than approximately 4%. A synergistic relationship between the calcium content and the potassium (or sodium) content is described. An acetone refining step is employed in preparing the HCA extract. As previously mentioned, potentially toxic residues of chemicals employed during manufacture may be a concern in some HCA compositions intended for consumption.

There exists a need for a pure, stable, highly soluble formulation of HCA salts that addresses the above-identified problems and eminently lends itself for incorporation into consumables such as drinking water, beverages, nutraceuticals, power bars, ice cream, and the like. Such products are useful as diet aids to help with weight reduction. Also needed is a better and more commercially attractive way to prepare such HCA salt formulations.

BRIEF SUMMARY OF PREFERRED EMBODIMENTS

Improved methods of making compositions hydroxycitric acid salts that are very pure, water soluble and stable in solution and during storage are provided in accordance with certain embodiments of the present invention. Also provided are methods of using the resulting compositions as nutraceuticals, dietary supplements, functional additives in foods, beverages and even in clear, essentially tasteless drinking water.

In accordance with certain embodiments of the present invention, a simple, compact process for the production of a stabilized formulation of hydroxycitric acid salts is provided, preferably in very pure form. For the purposes of this disclosure, the term "high purity" refers to a product having a hydroxycitrate content of at least 70-75% and a lactone content of no more than 0.5% (by weight of the total weight of the product).

Certain embodiments of the invention provide a method or process for making a hydroxycitric acid salt composition that is eminently suited to commercial-scale manufacturing. The method includes preparing an aqueous extract of *Garcinia cambogia* or *Garcinia indica* fruits and extracting that aqueous extract with a liquid quaternizing agent to yield a quaternizing agent extract containing hydroxycitric acid. In preferred embodiments the quaternizing agent (QA) is a trialkylamine in which the alkyl groups are octyl, caprylyl, isooctyl, lauryl and decyl, or a combination of any of those groups. In certain embodiments the QA is tricaprylylamine.

In certain embodiments the method comprises treating the QA extract with potassium hydroxide or sodium hydroxide and recovering a potassium hydroxycitric acid salt solution or a sodium hydroxycitric acid salt solution. In certain embodiments the method comprises treating the potassium or sodium hydroxycitric acid salt solution with activated charcoal such that a decolorized potassium or sodium hydroxycitric acid salt solution is obtained.

In some embodiments the method includes preparing a decolorized sodium hydroxycitric acid salt solution and treating it with a calcium salt (calcium chloride, for example) such that a heterogeneous slurry comprising insoluble calcium hydroxycitric acid salt is obtained. Some embodiments include adjusting the pH of the slurry to a pH in the range of 9.5-11 such that a calcium hydroxycitric acid precipitate is obtained. In some embodiments the precipitate is then washed and dried to provide a powder comprising pure calcium hydroxycitrate.

In certain embodiments, the method includes a) preparing a calcium salt of hydroxycitric acid, as described above; b) preparing an aqueous solution comprising the potassium salt of hydroxycitric acid, as described above; c) dissolving the calcium HCA salt in the potassium HCA solution to provide a potassium-calcium hydroxycitric acid salt solution; and d) drying the potassium-calcium hydroxycitric acid salt solution to yield a powder comprising potassium and calcium hydroxycitric acid salts. A preferred way of drying the solution is spray drying, although another technique that is capable of providing an equivalent powder could be substituted.

In certain preferred embodiments the method includes combining the calcium hydroxycitric acid salt and the potassium hydroxycitric acid salt solution in a molar ratio in the range of about 1.9-2.9 calcium hydroxycitric acid salt: about 0.9-1.4 potassium hydroxycitric acid salt. In a more preferred embodiment equivalent molar amounts of the potassium hydroxycitric acid salt solution and the calcium salt of hydroxycitric acid are combined.

In some embodiments the method includes reducing the resulting powder to about 80 mesh size particles. This may be done by pulverizing or any other suitable method that produces about the same size particles.

In still other embodiments of the present invention, a hydroxycitric acid salt composition is provided which is the product of a method as described above. In some embodiments, the product comprises a potassium or sodium hydroxycitric acid salt composition. In some embodiments the product comprises a calcium hydroxycitric acid salt composition which contains about 72 wt % hydroxycitrate, about 17 wt % calcium, and about 10 wt % water.

In another embodiment the composition contains defined proportions of a potassium salt of HCA (e.g., potassium, 11-18%) and a calcium salt of HCA (e.g., calcium 5-10%) to yield a stabilized (i.e., non-hygroscopic, readily soluble) mixture. One highly preferred composition prepared as described above contains 72% HCA, 9% calcium, 14% potassium, 4% structural moisture, 0.5% sodium and 0.5% lactone. Percentages are calculated on the basis of gravimetric quantities of each component in the total salt.

In certain embodiments the composition contains 70-75 wt % hydroxycitrate, 7.5-9.5 wt % calcium, 12-15 wt % potassium, no more than 0.5 wt % of the lactone form of hydroxycitric acid, and up to 0.5 wt % moisture. In some embodiments the composition has a room temperature solubility of at least 5 g in 100 mL water, and is capable of yielding a clear, tasteless, transparent solution in water. With this high solubility the preferred compositions are especially suited for use in a variety of food items, such as beverages, ice cream, candy and drinking water. Food or drinks containing the preferred calcium-potassium HCA composition avoid the unpleasant pungent taste of potassium that is typically associated with other potassium HCA-containing products. Such HCA salt containing products are effective dietary aids for use in weight loss programs.

Accordingly, certain embodiments of the invention provide a precipitate-free aqueous solution that contains the above described potassium and calcium HCA salt composition. In other embodiments a food, beverage or dietary supplement is provided that contains the above described potassium and calcium HCA salt composition.

In still other embodiments of the present invention, a method of reducing body weight is provided. The method includes administering to an individual in need of weight reduction an effective amount (e.g., up to 5 g/kg of body weight of the composition per day).

These and other embodiments, features and advantages of the present invention will become apparent with reference to the following description and drawings.

DETAILED DESCRIPTION OF PREFERRED EMBODIMENTS

Figure 1:
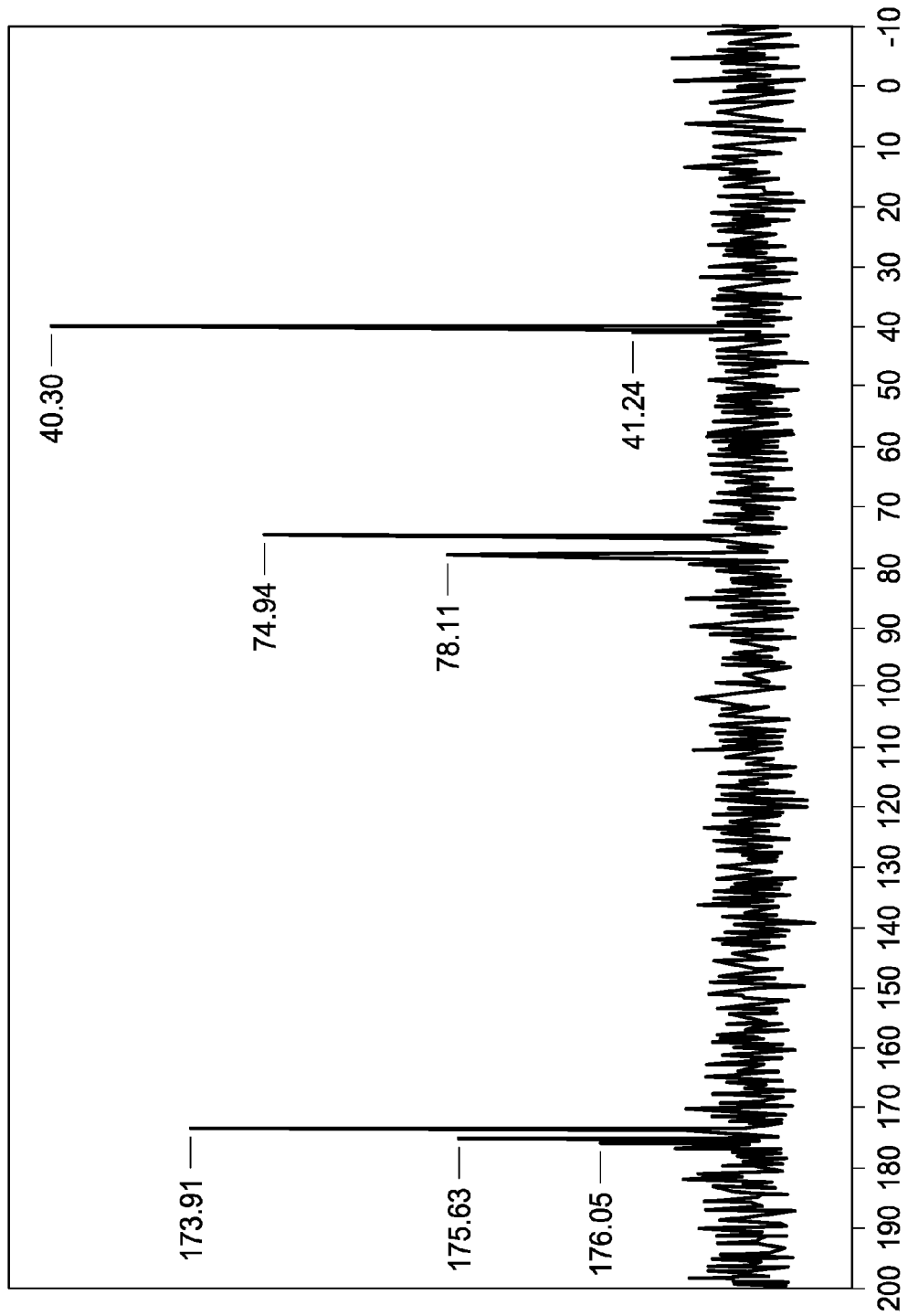
FIG. 1 is a proton NMR spectrum of the mixed salts of calcium and potassium hydroxycitric acid prepared in accordance with one embodiment of the present invention.

The process for making a very pure potassium-calcium HCA salt mixture generally includes preparing an aqueous potassium HCA salt solution, preparing a dried pure calcium HCA salt, and then combining the dry calcium HCA salt with the liquid potassium HCA salt solution, as described in more detail as follows:

Preparation of Potassium Salt of Hydroxycitric Acid

Garcinia cambogia or Garcinia indica fruits are procured and extracted with demineralized water equivalent to 12 to 20 volumes on the fruit, and the resulting juice is filtered to remove all the suspended plant materials. The clear, filtered juice is then loaded on a stainless steel column, preferably having a tubular structure. From the bottom of the tube, a quaternizing agent (QA) such as a liquid trialkylamine is passed in a counter current manner at a predetermined rate so as to have a QA residence time of 1 to 10 min. The desired residence time can be achieved by controlling the flow at the inlet of the column. The upper (QA) extract is continuously removed and taken into a vessel for the recovery of the Garcinia acid. Preferred trialkylamines have octyl, caprylyl, isooctyl, lauryl or decyl groups or a combination of any of those groups, as the amine substituents. Tricaprylylamine is especially preferred.

The collected QA extract layers are combined and treated with a solution of 0.5 N potassium hydroxide under agitation for a period of time ranging from about 10-100 minutes. After extracting the solution for the desired time the layers are separated. The clear bottom layer containing the potassium hydroxycitrate is removed and treated with activated charcoal to remove the coloring impurities. The amount of activated charcoal employed in the treatment depends upon the amount of color in the extract. During activated charcoal treatment the solution needs to be heated to a temperature in the range of about 75-95° C., preferably about 90° C., and maintained at that temperature for about 30 to 80 minutes, preferably about 60 minutes, and then hot filtered. The resulting clear filtrate contains the potassium salt of hydroxycitric acid of a strength varying from 0.3N to 0.5N in aqueous solution. This solution is reserved for mixing with other ingredients before stabilization and spray drying.

Preparation of Calcium Salt of Hydroxycitric Acid

For making the calcium salt of hydroxycitric acid, the above-described process is modified in the following manner. A fresh lot of fruits is extracted with demineralized water and filtered to remove all the suspended plant materials, the clear filtered juice is loaded on a stainless steel column and extracted with the quaternizing agent as previously described. The collected QA extract layers are combined and treated with a solution of 0.5N sodium hydroxide under agitation for 10-100 minutes. After extracting the solution for the desired time, the layers are separated. The clear bottom layer containing the sodium hydroxycitrate is removed and treated with activated charcoal to remove the coloring impurities. Again, the amount of activated charcoal used can vary, depending upon how extensively colored the extract is. During the activated charcoal treatment the solution is heated and then hot filtered, as described above. The clear filtrate contains the sodium salt of hydroxycitric acid of a strength ranging from 0.3N to 0.5N in aqueous solution. Preferably the QA layer is recovered and recycled for use in subsequent extractions.

The solution containing the sodium salt of hydroxycitric acid is treated with a stoichiometric amount of calcium chloride solution in demineralized water. The resultant solution is mixed for 30-120 minutes. Initially a lean precipitate appears which on standing becomes thick. The pH of the heterogeneous slurry is adjusted to 9.5 to 11, preferably about pH 10, using a 10% sodium hydroxide solution. The slurry is then filtered and washed with demineralized water to remove all adhering salts. The washings are monitored for chlorides, and washing is continued until the filtrate is chloride free. The wet cake is dried in a vacuum oven at a temperature between 70° C. and 100° C., preferably at 85 C. The resultant dried powder, which is preferably at least 99% pure salt of calcium hydroxycitrate, is pulverized to obtain a uniform powder of 80 mesh size (about 0.177 mm sieve opening. See Tyler Standard Screen Scale, in C. J. Geankoplis, TRANSPORT PROCESSES AND UNIT OPERATIONS, Allyn and Bacon, Inc., Boston, Mass., p. 837).

Combination of the Potassium and Calcium Salts of Hydroxycitric Acid

Preferably an equal quantity (stoichiometric to the acid content) of the potassium salt solution prepared as described above) and the dry calcium salt are mixed to yield a clear liquid. The resultant liquid is treated with activated charcoal again, if necessary, to provide a colorless solution. This solution is then spray dried to yield a free flowing white powder. The product is characterized by good water solubility, stability during storage and reduced hygroscopic property compared to most conventional hydroxycitric acid salt preparations. Moreover, the calcium stabilizes the potassium component to avoid the problems commonly associated with the hygroscopic nature of potassium hydroxycitrate. The potassium-calcium HCA salt combination resists clumping of the dry mixture, and overcomes many of the disadvantages of prior HCA salt preparations. This stabilized potassium and calcium HCA salt composition is suitable for use in drinking water, beverages, ice cream, candy, power bars and other food items without materially changing the original flavor, color and fragrance of any of the principal food items, and without imparting a noticeable pungency or bitterness that is usually associated with potassium-containing HCA preparations. The product was analyzed for the presence of residual quaternizing agent and none was detected.

While various compositions containing the salts of HCA are known, the present inventors discovered unexpectedly good results when equal amounts (with respect to HCA content) of the potassium and calcium salts, prepared as described above, are combined in the product (i.e., a 2:1 molar ratio of (K)HCA:(Ca)HCA). This particular combination of calcium and potassium salts was found to be superior for use in aqueous solutions of the product. Although the 2:1 molar ratio provides a superior, highly preferred product, it was determined that is also possible to obtain unexpectedly good hygroscopic property, solubility, stability, taste, and other desirable properties using molar ratios in the range of 1.9-2.9 (K)HCA:0.9-1.4 (Ca)HCA. Outside of this range the combined salts lack the advantageous combination of desirable properties that make it better suited for inclusion in food products, dietary supplements, nutraceuticals and especially for use in clear drinking water or other beverages in which cloudiness or precipitates are unacceptable. The special advantages or criticality of this range of molar ratios, especially the stoichiometric 2:1 ratio described above, has not previously been recognized.

EXAMPLE 1

Calcium Salt of Hydroxycitric Acid 500 g of salt-free Garcinia cambogia fruit rinds were extracted with 700 ml of hot deionized water at 70 to 75° C.

for 20 minutes in a percolator. The spent rinds were subsequently extracted with 400 ml of hot deionized water twice, and all the extracts were combined and filtered through nylon cheesecloth. The clear filtrate measured 1000 ml, having an acid content of 6.5% (as hydroxycitric acid). This solution was taken in a tubular glass or stainless steel column, with a bottom liquid sparging arrangement, connected with a non-return valve. Through the bottom line 400 g of tricaprylyl amine, which is a liquid quaternizing agent (QA), was pumped using a dosing pump. The flow rate of the liquid was adjusted in such a manner as to achieve a column liquid contact time of 1 minute (approximately 3 ml/min of tricaprylyl amine). The top extract was removed and taken into a container. The QA layer was washed with deionized water and the wash water discarded.

37.5 g of sodium hydroxide pellets was dissolved is 400 ml of water. This alkali solution was mixed with the QA extract and stirred for 30 minutes. Layers were separated and the top QA layer was taken for reuse after a water wash to remove the acidity. The alkaline extract was treated with 75 grams (g) of activated charcoal and the solution was heated to 90° C. The solution was filtered clear and treated with calcium chloride solution (52 g in 100 mL water). The pH of the solution was adjusted to 8.5 using 5% sodium hydroxide solution, the resulting precipitate was filtered, washed with deionized water free of chlorides and dried in a vacuum oven at 70° C. The weight of the resulting compound was 70 g. High performance liquid chromatography (HPLC) analysis was employed in determining the chemical makeup of the resulting calcium hydroxycitric acid salt. Briefly, the procedure included subjecting the sample to ion exchange chromatography, both quantitative and using reverse phase C-18 columns. The free hydroxycitric acid released by elution through the cation exchange resin was measured by HPLC according to the procedure described by P. Kucera et al., DIFFERENTIAL FRONTAL ANALYSIS OF CARBOXYLIC ACIDS, J. Chromatography (1981) 210:373-388), the disclosure of which is incorporated herein by reference. The hydroxycitric acid content was found to be 72.5%, as indicated in Table 1.

TABLE 1

PROXIMATE ANALYSIS

| | |
|---|---|
| Hydroxycitric acid content | 72.5% by HPLC |
| Calcium content | 17.22% by atomic absorption |
| Water content | 10% by TGA |
| TOTAL | 99.72% |

EXAMPLE 2

Potassium Salt of Hydroxycitric Acid

The above procedure was repeated with a fresh lot of Garcinia fruit, except that instead of using NaOH, the QA extract solution was treated with 61.9 g of potassium hydroxide (85%) in 400 ml of water. The extracted potassium hydroxide layer was treated with activated charcoal at 90° C. and the resulting filtrate was clear. This solution contained about 82.3 g of potassium hydroxycitrate.

EXAMPLE 3

Combined Potassium-Calcium Salts of Hydroxycitric Acid 50 g equivalent of the hydroxy citric acid—potassium salt solution from Example 2 was taken into a glass beaker fitted with a stirring arrangement. To this solution, 43 g of the dried calcium salt from Example 1 was added and the mixture was stirred to yield a clear solution. The resultant solution was spray dried to yield a salt of hydroxycitric acid with the following analysis: potassium content 11% to 18%, calcium content 5% to 12%, structural moisture 3% to 5% and hydroxycitric acid content 70% to 76%. The sodium content was less than 0.5% and lactone less than 0.5%. The combined salt has a solubility of 5 g in 100 mL of deionized water at room temperature. This salt composition is tasteless and white in color. A solution of 5 g in 100 ml of de-ionized sterile water was subjected to an accelerated storage study chamber for 2 months. After 2 months it was observed that the salt did not precipitate out. The solution retained its clarity. Therefore, it can be safely concluded that, after dissolution in water, the salt composition does not decompose during storage.

Structural Analysis of the Calcium-Potassium Hydroxycitric Acid Salt

A detailed structural study of the resulting representative product was performed with H-NMR and $C^{13}$NMR. The results are summarized below, in Tables 2-4 and in FIGS. 1 and 2. Calcium, potassium and sodium content was estimated by atomic absorption using conventional methods and apparatus. The calcium content of a representative sample was found to be 9%. The potassium content by this method was 14% and the sodium content was 0.5%.

The $C^{13}$NMR spectrum for the calcium-potassium hydroxycitric acid salt is shown in FIG. 1, and summarized in Table 2. The respective carbon atoms are indicated on the chart. There are three quaternary carbons appearing at chemical shift: 40.3, 74.9, 78.1 and carbonyl carbons at the chemical shift: 173.9, 175.5, 176.05 confirming the structural carbons of hydroxycitric acid in the sample.

TABLE 2

$C^{13}$ NMR

| Chemical shift | Assignment |
|---|---|
| 40.3 | Methylene carbon (—$CH_2$—) |
| 74.94 | Methine carbon (—CH—) |
| 78.11 | Quaternary carbon (—C—) |
| 173.9, 175.53, 176.05 | Carbons of acid carbonyl |

Figure 2:
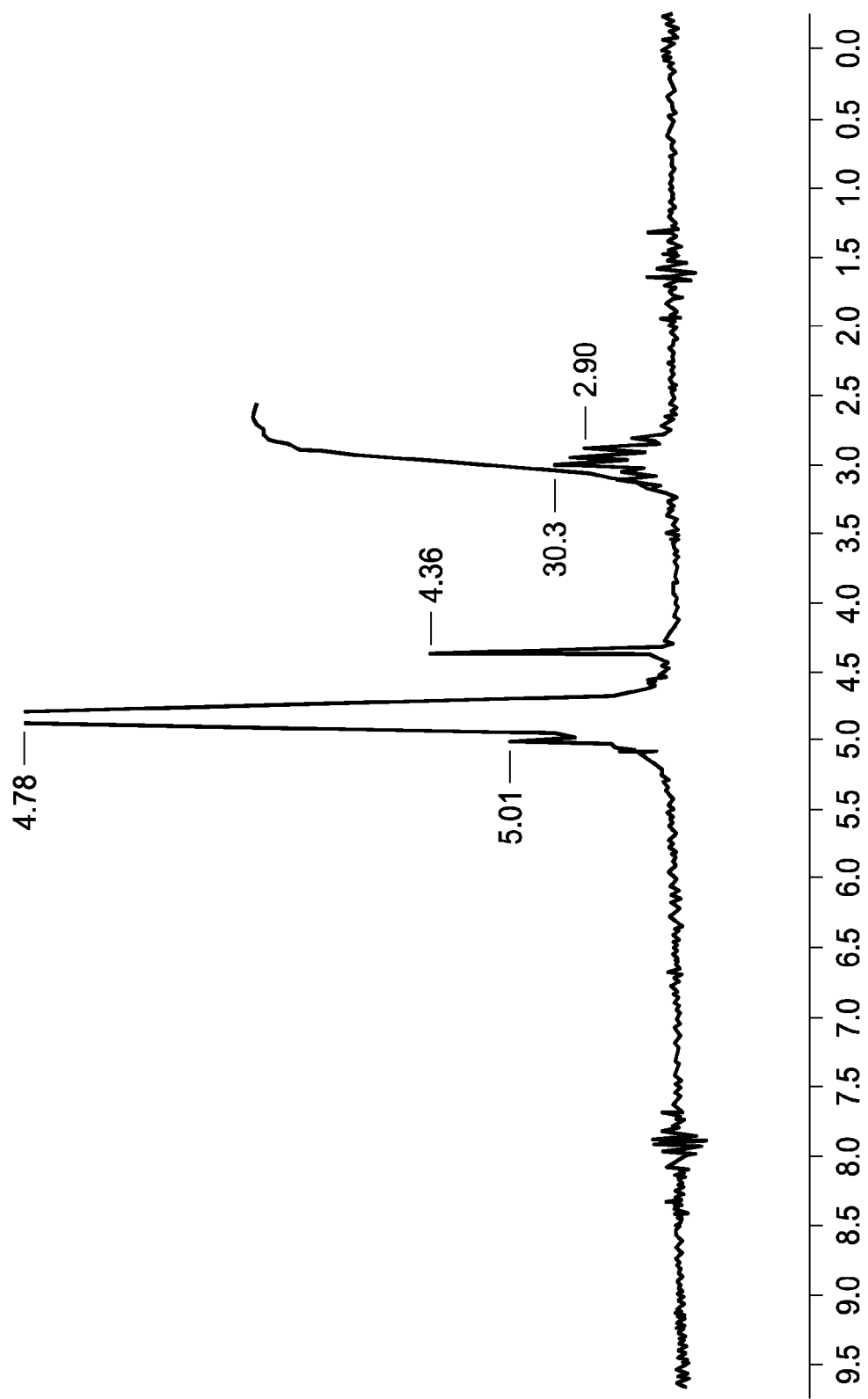
FIG. 2 is a $C^{13}$-NMR spectrum of the mixed salts of calcium and potassium hydroxycitric acid prepared in accordance with one embodiment of the present invention.

The proton NMR spectrum for the HCA salt is shown in FIG. 2, and summarized in Table 3. The acid protons and hydroxy protons are not visible due to $D_2O$ exchange.

TABLE 3

PROTON NMR

| Chemical shift (ppm) | Assignment | No. |
|---|---|---|
| 2.5-3.5 (multiplet) | —CH$_2$— | two protons |
| 4.35 (singlet) | —CH— | single proton |
| 4.75 (off scale large peak) | HOD D$_2$O exchanged structural water | |

Frequency: 300 MHZ
Nucleus: 1 H
Solvent: D$_2$O (Since the material was a salt & insoluble in all deuterated solvents like acetone - D6, DMF - D6, chloroform - D, C it was decided to use water - D2.) By this method all exchangeable protons will not be seen in the NMR spectra.

Animal Toxicity Study

A representative lot of powder obtained as described above is a pure, stable calcium potassium salt of hydroxycitric acid having a proximate analysis of 70 to 75% hydroxycitric acid, 7.5% to 9.5% calcium, 12 to 15% potassium and 3 to 5% structural moisture. The sodium content is less than 0.5%, and HCA lactone content is less than 0.5%. An animal toxicity study was conducted on the product to establish its LD$_{50}$. The LD$_{50}$ of a representative sample was found to be more than 5 gm/kg in female Wistar rats. The protocol for the study is summarized in Table 5 and as follows:

TABLE 5

REPORT ON LD$_{50}$ OF TEST COMPOUND

| Sr. No. | Name | Description |
|---|---|---|
| 1 | Test Compound | White Fine Powder |
| 2 | Solubility | Soluble In Water |
| 3 | Method of Testing | Acute Oral Toxicity (OECD Test Guideline 425) Statistical Program |

Doses were selected in accordance with the Acute Oral Toxicity (OECD Test Guideline 425) Statistical Program as follows: 175, 550, 1750, 5000 mg/kg of body weight in adult female Wistar rats.

TABLE 6

Protocol for Animal Toxicity Study

| Test/Substance: | Test Compound |
|---|---|
| Test type: | Main Test |
| Limit dose (mg/kg): | 5000 |
| Assumed LD50 (mg/kg): | Default |
| Assumed sigma (mg/kg): | 0.5 |
| Recommended dose progression: | 1.75, 5.5, 17.5, 55, 5000, 175, 550, 1750 |

TABLE 7

Animal Toxicity Data

| Test Seq. | Animal ID | Dose (mg/kg) | Short-term Result | Long-term Result |
|---|---|---|---|---|
| 1 | H | 175 | ○ | ○ |
| 2 | B | 550 | ○ | ○ |
| 3 | T | 2000 | ○ | ○ |
| 4 | HB | 5000 | ○ | ○ |
| 5 | HT | 5000 | ○ | ○ |
| 6 | BT | 5000 | ○ | ○ |

(X = Died, ○ = Survived)
Dose Recommendation: The main test is complete.
Stopping criteria met: 3 at Limit Dose.

TABLE 8

Summary of Long-Term Animal Toxicity Test Results

| Dose (mg/kg) | Survived | Died | Total |
|---|---|---|---|
| 175 | 1 | 0 | 1 |
| 550 | 1 | 0 | 1 |
| 2000 | 1 | 0 | 1 |
| 5000 | 3 | 0 | 3 |
| All Doses | 6 | 0 | 6 |

Conclusion: LD$_{50}$ of a sample of the Test Compound was found to be greater than 5000 mg/kg.

Dietary Aids for Weight Reduction Programs

The above-described calcium and potassium hydroxycitric acid salt compositions are useful in any of a variety of forms, including conventional pharmaceutical preparations and dietary supplements. For instance, they can be mixed with conventional organic or inorganic inert pharmaceutical carriers or dietary supplements suitable for oral or parenteral administration, such as, for example, water, gelatin, lactose, starch, magnesium stearate, talc, vegetable oil, gums or the like. They can be administered in conventional forms, e.g., solid forms, for example powders, tablets, capsules, suppositories or the like; or in liquid forms, for example, suspensions or emulsions. Optionally, these compositions can be subject to conventional pharmaceutical or dietary supplements expedients, such as sterilization, and can contain conventional pharmaceutical or dietary supplements excipients, such as preservatives, stabilizing agents, emulsifying agents, salts for the adjustment of osmotic pressure of buffers, and the like. The compositions can also be advantageously combined with other therapeutically active materials.

In addition, the above-described compositions can be formulated as a part of a processed food product for example in the form of a bar, baked good, beverage, drinking water, ice cream, candy or other item of food, using conventional techniques. Because the preferred calcium-potassium HCA salt composition can be dissolved in water to provide a clear, essentially tasteless, transparent solution, one of the more preferred forms of administration is in drinking water.

Whether administered as a food or drink, a suitable dosage unit for a mammal is generally about 15 mg to about 3 g of hydroxycitric acid, administered up to three times per day. For example, a suitable eternal dosage regimen in a mammal may range from about 1 mg per kilogram of body weight to about 50 mg per kilogram of body weight per day. For a particular subject, however, the specific dosage regimen can be adjusted according to individual need and the professional judgment of the person administering or supervising the administration of product.

For aiding a typical weight loss program, an orally administered food product, such as drinking water, a flavored beverage or a power bar containing an above-described calcium-potassium hydroxycitric acid composition will preferably make up above 0.001 to 25%, preferably 0.05 to 5% by weight of the total weight of the food product.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims. The disclosures of all patents, patent applications and publications cited herein are hereby specifically incorporated herein by reference, to the extent that they provide materials, methods or other details supplementary to those set forth herein.

What is claimed is:

1. A method of making a hydroxycitric acid salt composition comprising:
   (a) preparing an aqueous extract of *Garcinia cambogia* or *Garcinia indica* fruits and extracting said aqueous extract with a liquid quaternizing agent comprising a trialkylamine in which the alkyl groups are selected from the group consisting of octyl, caprylyl, isooctyl, lauryl, decyl and combinations thereof, to yield a quaternizing agent extract that contains hydroxycitric acid;
   (b) treating said quaternizing agent extract with potassium hydroxide or sodium hydroxide and recovering a potassium hydroxycitric acid salt solution or a sodium hydroxycitric acid salt solution;
   (c) treating said potassium or sodium hydroxycitric acid salt solution with activated charcoal such that a decolorized potassium or sodium hydroxycitric acid salt solution is obtained;
   (d) treating said decolorized potassium or sodium hydroxycitric acid salt solution with a calcium salt such that a heterogeneous slurry comprising insoluble calcium hydroxycitric acid salt precipitate is obtained, wherein said treating comprises adjusting the pH of said decolorized solution to a pH in the range of 9.5-11;
   (e) washing and drying said precipitate to yield a powder comprising the calcium salt of hydroxycitric acid;
   (f) obtaining an aqueous solution comprising the potassium salt of hydroxycitric acid, prepared as in (a)-(c);
   (g) dissolving said powder comprising the calcium salt of hydroxycitric acid in said potassium hydroxycitric acid salt solution to provide a potassium-calcium hydroxycitric acid salt solution, wherein said dissolving comprises combining said calcium hydroxycitric acid salt and said potassium hydroxycitric acid salt solution in a molar ratio in the range of about 1.9-2.9 calcium hydroxycitric acid salt: about 0.9-1.4 potassium hydroxycitric acid salt;
   (h) drying said potassium-calcium hydroxycitric acid salt solution to yield a powder comprising a mixture of potassium hydroxycitric acid salt and calcium hydroxycitric acid salt.

2. The method of claim 1 comprising reducing said powder to about 80 mesh size particles.

3. The method of claim 1 wherein said trialkylamine is tricaprylylamine.

4. The method of claim 1 wherein said calcium salt is calcium chloride.

5. The method of claim 1 wherein said powder comprising the calcium salt of hydroxycitric acid contains about 72 wt % hydroxycitrate, about 17 wt % calcium, and about 10 wt % water.

* * * * *